United States Patent [19]
Idemoto et al.

[11] Patent Number: 5,205,817
[45] Date of Patent: Apr. 27, 1993

[54] SURGICAL INSTRUMENT

[75] Inventors: Morito Idemoto; Naohiko Inoue; Yasuo Noguchi, all of Yokohama, Japan

[73] Assignee: Sumitomo Bakelite Company Limited, Tokyo, Japan

[21] Appl. No.: 820,859

[22] PCT Filed: May 17, 1990

[86] PCT No.: PCT/JP90/00627
§ 371 Date: Jan. 17, 1992
§ 102(e) Date: Jan. 17, 1992

[87] PCT Pub. No.: WO91/17716
PCT Pub. Date: Nov. 28, 1991

[51] Int. Cl.⁵ .................................. A61B 17/20
[52] U.S. Cl. ...................... 604/22; 128/24 AA; 606/169
[58] Field of Search .............. 128/24 AA; 604/22; 606/169-171, 159

[56] References Cited
U.S. PATENT DOCUMENTS

| | | | |
|---|---|---|---|
| 2,874,470 | 2/1959 | Richards | 604/22 |
| 3,589,363 | 6/1971 | Banko et al. | 604/22 |
| 4,188,952 | 2/1980 | Loschilov et al. | 604/22 |
| 4,561,438 | 12/1985 | Bonnet et al. | 604/22 |
| 4,634,419 | 1/1987 | Kriezman et al. | 604/22 |
| 4,832,683 | 5/1989 | Idemoto et al. | 604/22 |
| 4,959,049 | 9/1990 | Smirmaul | 604/22 |
| 4,978,333 | 12/1990 | Broadwin et al. | 604/22 |

FOREIGN PATENT DOCUMENTS

| | | |
|---|---|---|
| 48-15110 | 5/1973 | Japan . |
| 50-91188 | 7/1975 | Japan . |
| 60-192807 | 12/1985 | Japan . |
| 62-224345 | 10/1987 | Japan . |

Primary Examiner—Stephen C. Pellegrino
Assistant Examiner—Michael Rafa
Attorney, Agent, or Firm—Browdy and Neimark

[57] ABSTRACT

A surgical instrument comprises an ultrasonic source (7) and an ultrasonic vibration transmitter (8) connected to the source (7), which generates ultrasonic mechanical vibration. The ultrasonic vibration transducer includes a plurality of ring-shaped cutting blade portions (14) provided on an outer periphery of an operational part (9) which contacts organic tissue, and a liquid passage (11) through the transducer. The liquid passage opens at a front end (12) of the operational part and at recesses (13) between the blade portions. The surgical instrument cuts or incises organic tissue by ultrasonic vibration.

4 Claims, 3 Drawing Sheets

SURGICAL INSTRUMENT

TECHNICAL FIELD

The present invention relates to a surgical instrument which cuts organic tissue by ultrasonic vibration.

BACKGROUND ART

Kerrison forceps, alveolar-bone forceps, scalpels, gouges (cylindrical chisels), files, surgical bars, etc. have been used for cutting organic tissue, particularly hard tissue, in neurosurgery, orthopaedic surgery, plastic surgery, oral surgery, etc. However, cutting with scalpels, forceps such as Kerrison forceps, etc. is inefficient, requiring long hours of operation, substantial labor of an operator and highly developed skill in the case of a fine cutting operation. Surgical bars driven by air pressure have a problem in that because a drill is rotating during an operation, shaking occurs at a contact location between a bar and hard tissue and is transmitted to the hand of the operator, thus making a fine and delicate operation difficult. Also, organic tissue at a cut surface is likely to lose its activity because of frictional heat caused by the rotational cutting. Further, because of rotational movements of the drill, a surgical bar will damage vascular or neural tissue in organic tissue even by a slight touch thereto.

Surgical instruments using ultrasonic have previously been developed. There are known a surgical instrument which destroys contacting organic tissue by ultrasonic vibration of an ultrasonic vibration transmitter and then sucks to remove the destroyed tissue (disclosed, for example, in JP-B-47-39197) and a surgical instrument for incision of hard and soft organic tissue, which comprises a metallic operational part having a cutting edge (disclosed, for example, in JP-B-51-46990). However, the former surgical instrument is unsuitable for cutting to form a surface or to form or enlarge a hole because a vibrator including an operational portion having a flat surface perpendicular to the direction of vibration destroys and emulsifies a surface layer of soft organic tissue by ultrasonic vibration and sucks to remove the emulsified tissue. The latter surgical instrument incises organic tissue by a cutting edge vibrating ultrasonically. The frictional heat is generated between an operational portion and organic tissue being incised due to the vibration of the operational portion having a minimum amplitude, about 30 to 50 μm, required for incision. Therefore, even when an operational portion is made of a titanium alloy having a favorable heat conductivity, the surface temperature thereof rises to several hundred degrees Celsius, so that the organic tissue at the incision surface becomes carbonized. Also, the shape of the operational portion of the latter instrument is not suitable for cutting operation.

The present invention is aimed at solving these problems of the above-mentioned conventional surgical instruments. It is an object of the present invention to provide a surgical instrument for cutting organic tissue, which has improved cutting efficiency and operational precision, can prevent the deterioration of organic tissue caused by frictional heat generated between an operational portion and the organic tissue cut by the operational portion, and can minimize the loss of the mechanical strength of the operational portion caused by heat generated during operation.

DISCLOSURE OF THE INVENTION

In order to achieve the above object, the present invention provides a surgical instrument comprising an ultrasonic transmitter which is connected to an ultrasonic source and generates ultrasonic mechanical vibration and which includes a plurality of ring-shaped cutting-edge portions formed on a periphery of an operational part thereof which contacts organic tissue, and a liquid passage extending therein and having openings at a front end of said operational part and at a recess between the ring-shaped cutting-edge portions.

THE BEST MODE FOR CARRYING OUT THE INVENTION

Figure 1:
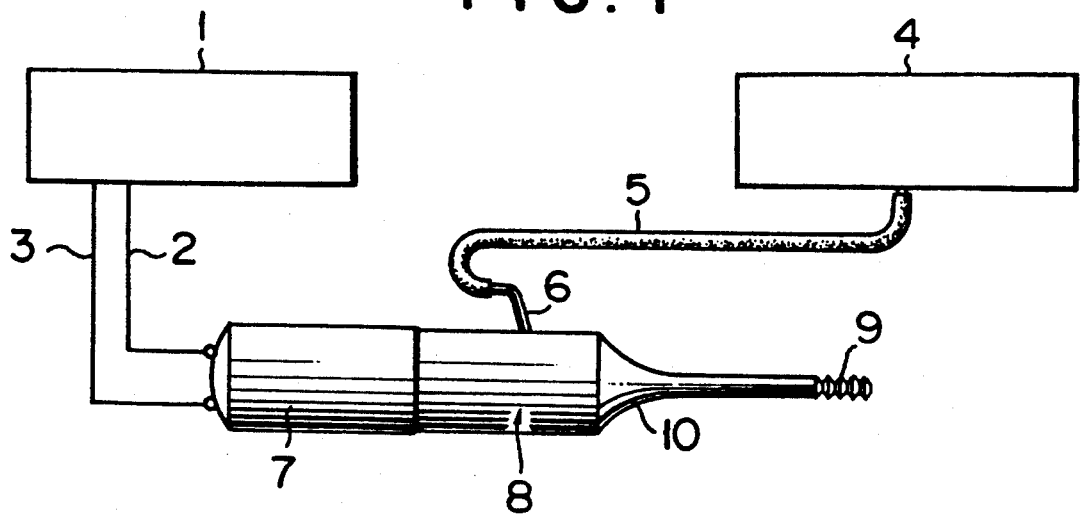
FIG. 1 is a block diagram of a surgical system employing a surgical instrument according to one embodiment of the present invention.

As shown in FIG. 1, a surgical instrument according to the present invention comprises an ultrasonic source 7 and an ultrasonic transmitter 8 having an operational portion 9. An ultrasonic oscillation circuit 1 sends ultrasonic electric signals through cables 2, 3 to the ultrasonic source 7. The ultrasonic source 7 generates mechanical ultrasonic vibration. The ultrasonic source 7 may be either a magnetostriction type or an electrostriction type. The mechanical ultrasonic vibration generated by the ultrasonic source 7 is transmitted to the ultrasonic transmitter 8. It is amplified at a connecting portion 10 of the ultrasonic transmitter 8 and then transmitted to an operational part 9. The operational part 9 directly contacts and cuts organic tissue by mechanical ultrasonic vibration.

Figure 2A:
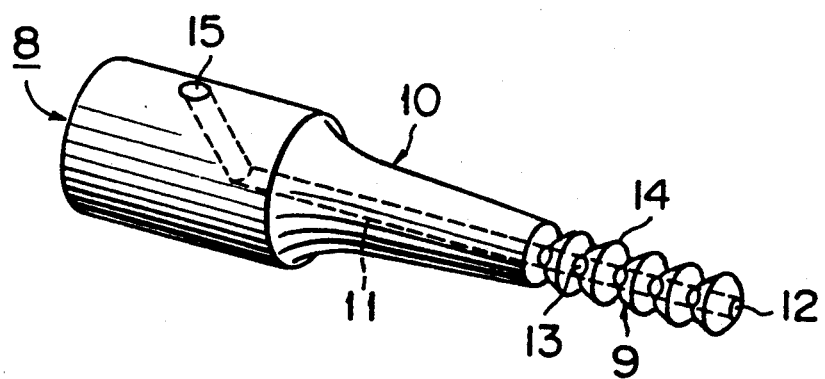
FIG. 2A is a perspective view of the instrument shown in FIG. 1.
Figure 2B:
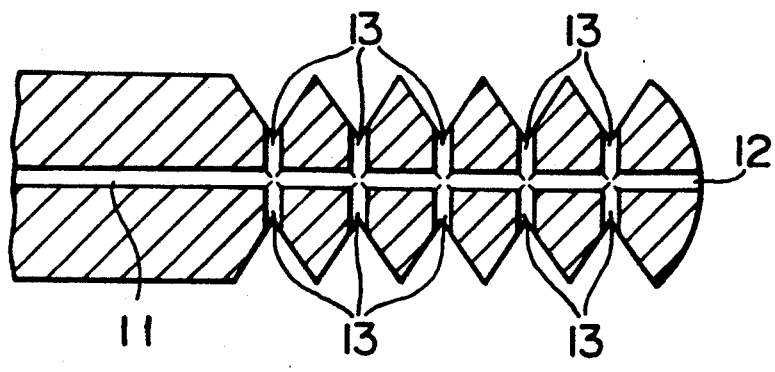
FIG. 2B is an enlarged fragmentary sectional view of the instrument shown in FIG. 2A.

As shown in FIGS. 2A and 2B, the operational part 9 of the ultrasonic vibration transmitter 8 has several ring-shaped cutting blades 14 on its periphery. The number of the ring-shaped cutting blades is not restricted. The pitch between the cutting blades are preferably 1 to 3 mm. The depth of the recess therebetween are preferably about 0.1 to 1 mm.

A fluid passage 11 is formed inside the ultrasonic transmitter 8. One end of the fluid passage 11 opens at an inlet 15 formed on the periphery, and the other end thereof opens a jetting outlet 12 on the front end of the operational part 9 and at jetting outlets 13 at each of the recesses between the cutting blades.

When the operational part 9 is performing the mechanical ultrasonic vibration, a liquid injecting pump device 4 sends liquid to the ultrasonic transmitter 8 through a tube 5 and a pipe 6 connected to the inlet 15 of the ultrasonic transmitter 8. Although the kind of liquid is not restricted, a liquid which does not greatly affect an organic tissue, such as physiological salt solution, is preferable. The liquid from the pipe 6 goes through the inlet 15 and the fluid passage 11 and then is jetted out of the jetting outlets 12, 13 of the operational part 9.

Though diameters of the jetting outlets 12, 13 of the fluid passage 11 are not restricted, it is preferable that the diameter of outlet 13 be smaller than that of the diameter of fluid passage 11 in order to improve the efficiency of liquid jetting. The liquid cools the operational part 9 and the organic tissue adjacent the operating portion, preventing a substantial temperature rise of the operational part 9 due to frictional heat caused by the ultrasonic vibration cutting. Also, a liquid, such as physiological salt solution, flowing through the passage 11 substantially restrains the ultrasonic transmitter 8 from heat-generating during a continuous use, thus preventing the loss of mechanical strength of the ultrasonic transmitter 8. Though the material of the ultrasonic transmitter 8 is not restricted, a titanium alloy having great tensile and fatigue strengths is preferable.

Figure 3:
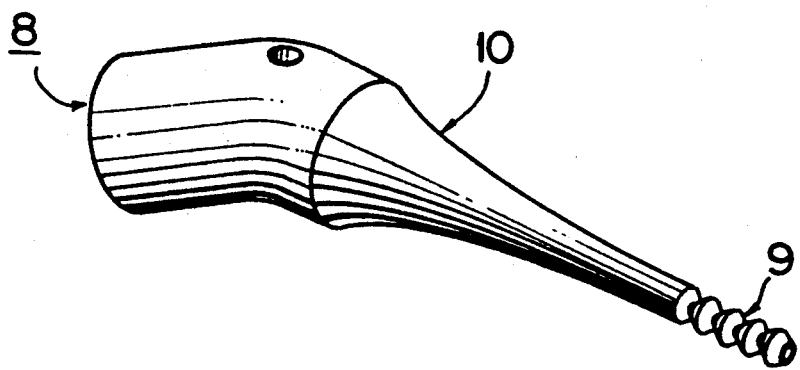
FIGS. 3 to 5 are perspective views of other embodiments of the present invention.
Figure 4:
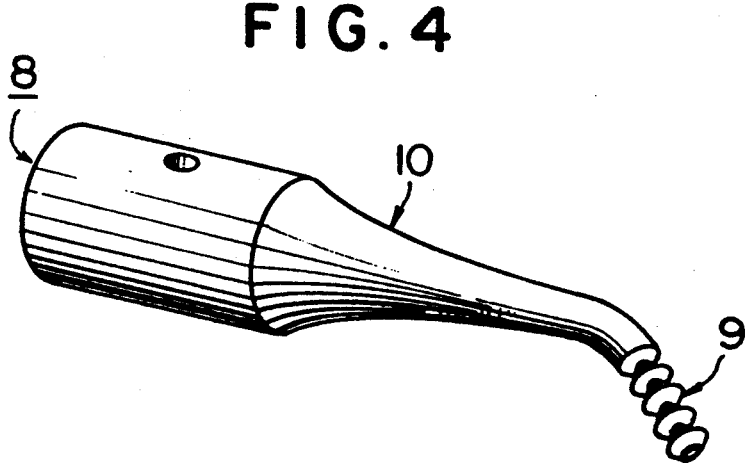
Figure 5:
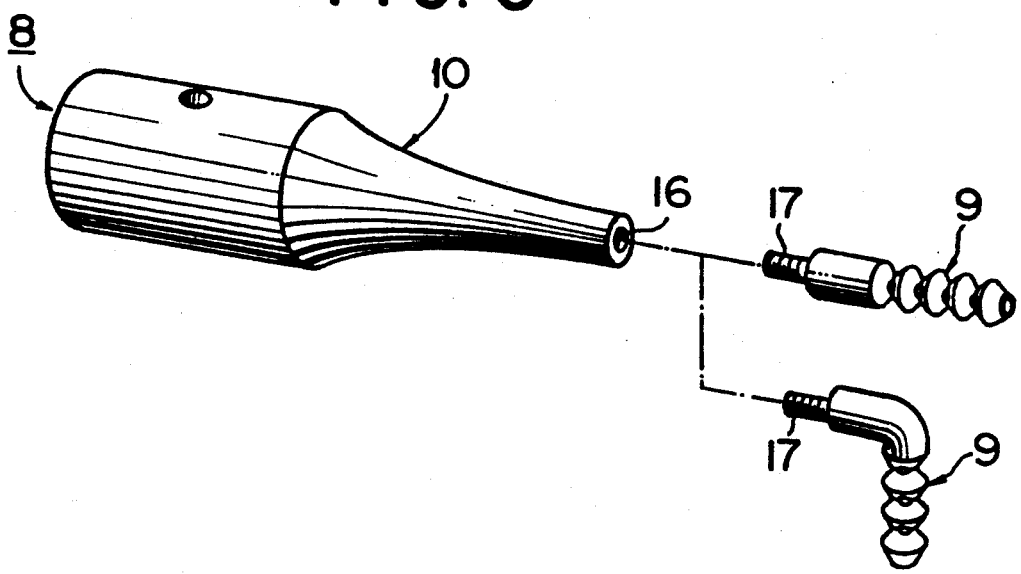

FIGS. 3 and 4 show other embodiments of the present invention which are suitable for cutting narrow or curved portions according to the operation technique employed. An ultrasonic transmitter 8 is bent at the rear of an intermediate portion 10 and/or at the rear of an operational part 9, so that the axis of the operational part 9 intersects the direction of the mechanical vibration of an ultrasonic vibration source. An angle of the intersection is in a range of 0° to 90°, preferably 0° to 60°. Further, as shown in FIG. 5, an operational part 9 may be connected to an ultrasonic transmitter 8 through a screw engagement between a female screw portion 16 and a male screw portion 17. Such construction is preferable because an operational part 9 can be exchangeable according to various uses.

The material for the operational part 9 is preferably a titanium alloy or a ceramics, particularly zirconia, silicon nitride or composite materials.

INDUSTRIAL APPLICABILITY

Figure 6A:
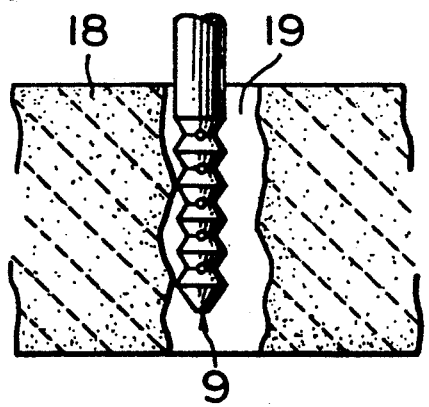
FIGS. 6A, 6B and 7 are views showing the use of a surgical instrument according to the present invention.
Figure 6B:
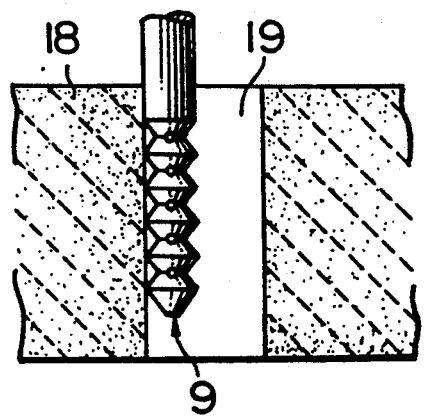
Figure 7:
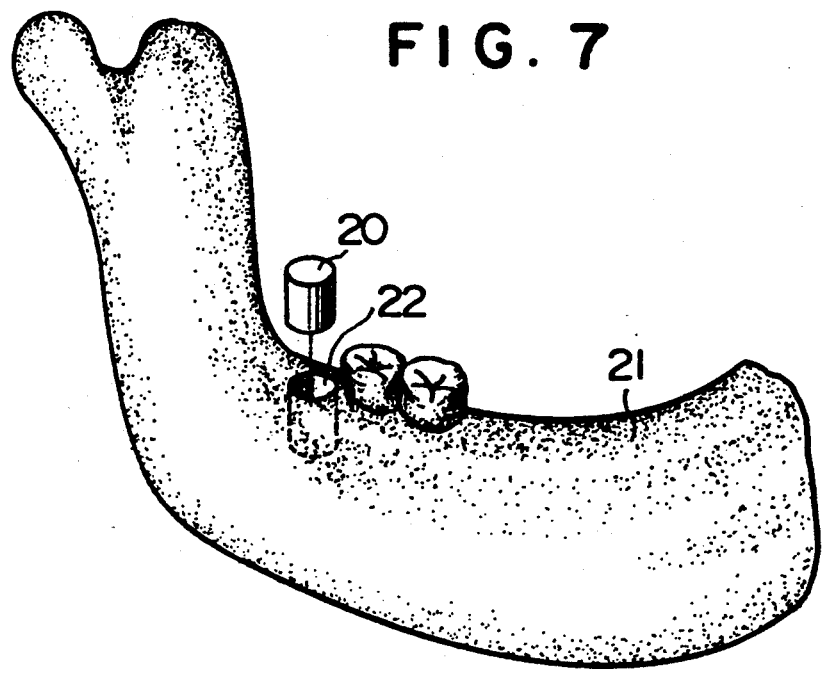

An application of a surgical instrument according to the present invention will be explained with reference to FIGS. 6A, 6B and 7. As shown in FIG. 6A, when the instrument according to the present invention is applied to an organic tissue 18, particularly to a rough interior surface of a hole 19 of a hard tissue, the operational part 9 cuts the rough interior surface to form a smooth surface as shown in FIG. 6B. FIG. 7 illustrates a specific case where after extraction of a tooth, an artificial dental root 20 is embedded in a lower jaw bone 21. In this case, a hole 22 for the artificial dental root 20 requires precise shaping. A surgical instrument according to the present invention can precisely smooth the rough wall and finish the hole precisely.

By using a surgical instrument according to the present invention, cutting of an organic tissue, particularly a hard tissue can be performed faster wit less skill required than by using a conventional instrument such as forceps. Also, since both the operational part performing the ultrasonic mechanical vibration and organic tissue are cooled during the operation, a deterioration of mechanical strength of the operational part due to frictional heat can be prevented, and organic tissue at a cutting surface thereof prevented from deteriorating so as to retain its activity. Further, since cutting is performed by ultrasonic vibration, without rotational movements as in a surgical bar, there is no danger that vascular or neural tissue may be whirled in or entangled during the operation. Thus, a surgical instrument according to the present invention is suitable for cutting organic tissue, particularly hard tissue.

We claim:

1. A surgical instrument for scraping or carving organic tissue by ultrasonic vibration, comprising an ultrasonic transmitter adapted to be connected to an ultrasonic source to generate ultrasonic mechanical vibration, a plurality of ring-shaped cutting blade portions provided at an interval of 1 to 3 mm on and surrounding a periphery of an operational part which contacts organic tissue, said operational part having a round cross section, each of said blade portions extending in a plane traversing a longitudinal axis of said operational part, and a liquid passage extending through said transmitter for supplying a liquid such as physiological salt water and opening at a front end of said operational part and at recesses each having a depth of 0.1 to 1 mm between said blade portions.

2. A surgical instrument according to claim 1, wherein said ultrasonic transmitter is bent at a rear of said operational part having said blade portions, so that an axis of said operational part intersects a direction of the mechanical vibration of an ultrasonic source.

3. A surgical instrument according to claim 1, wherein said operational part is removably mounted to said ultrasonic transmitter by a male and a female thread respectively located on said operation apart and said ultrasonic transducer.

4. A surgical instrument according to claim 1, wherein said ultrasonic transmitter is bent at a rear of a connecting portion between said ultrasonic transmitter and said operational part, so that an axis of said operational part intersects a direction of the mechanical vibration of an ultrasonic source.

* * * * *